United States Patent [19]
Bru-Magniez et al.

[11] Patent Number: 5,317,025
[45] Date of Patent: May 31, 1994

[54] PIPERIDINYLTHIOINDOLE DERIVATIVES, THEIR METHODS OF PREPARATION AND PHARMACEUTICAL COMPOSITIONS IN WHICH THEY ARE PRESENT, USEFUL ESPECIALLY AS ANALGESICS

[75] Inventors: Nicole Bru-Magniez, Paris; Dominique Potin, Aubergenville; Jean-Marie Teulon, La Celle Saint Cloud, all of France

[73] Assignee: Laboratoires UPSA, Agen, France

[21] Appl. No.: 81,704

[22] Filed: Jun. 25, 1993

[30] Foreign Application Priority Data

May 18, 1993 [FR] France ................................. 9305966

[51] Int. Cl.$^5$ .................. A61K 31/445; C07D 401/12
[52] U.S. Cl. ..................................... 514/323; 546/201
[58] Field of Search ......................... 546/201; 514/323

[56] References Cited
U.S. PATENT DOCUMENTS 3,264,311 8/1966 Szmuszkovicz ..................... 546/201

FOREIGN PATENT DOCUMENTS 925429 3/1961 United Kingdom ............... 546/201

Primary Examiner—C. Warren Ivy
Assistant Examiner—Celia Chang
Attorney, Agent, or Firm—Dennison, Meserole, Pollack & Scheiner

[57] ABSTRACT

The present invention relates to the derivatives of the formula

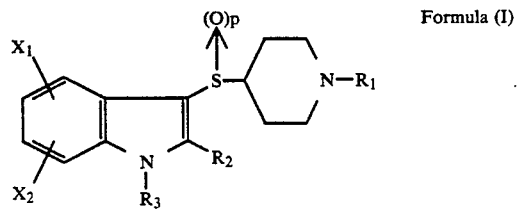

Formula (I)

and their addition salts, and to their use in therapeutics, especially as drugs having analgesic properties.

11 Claims, No Drawings

PIPERIDINYLTHIOINDOLE DERIVATIVES, THEIR METHODS OF PREPARATION AND PHARMACEUTICAL COMPOSITIONS IN WHICH THEY ARE PRESENT, USEFUL ESPECIALLY AS ANALGESICS

The present invention relates, by way of novel products, to the piperidinylthioindole derivatives of general formula (I) below and their addition salts, in particular the pharmaceutically acceptable addition salts.

The compounds in question have a very valuable pharmacological profile insofar as they possess analgesic properties. They will therefore be particularly indicated for the treatment of pain. There may be mentioned, for example, their use in the treatment of muscular, articular or neural algia, dental pain, herpes zoster and migraine, and in the treatment of rheumatic complaints and pain of cancerous origin, and also as complementary treatments in infectious and febrile states.

The present invention further relates to the method of preparing said products and to their applications in therapeutics.

These piperidinylthioindole derivatives have general formula (I):

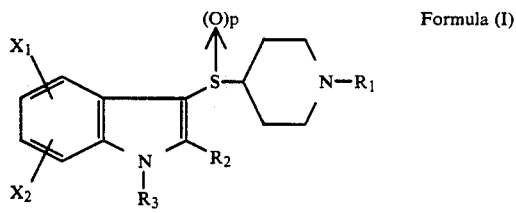

Formula (I)

in which:
$X_1$ and $X_2$ are independently:
  the hydrogen atom;
  a halogen atom;
  a lower alkyl radical having 1 to 6 carbon atoms;
  a trifluoromethyl group; or
  a lower O-alkyl radical having 1 to 6 carbon atoms;
  and can be located in the 4-, 5-, 6- or 7-position of the indole ring,
$R_1$ is:
  the hydrogen atom;
  a lower alkyl radical having 1 to 6 carbon atoms;
  a radical —$(CH_2)_n$-phenyl; or
  a radical —$(CH_2)_n$-pyrrole;
  in which n is an integer from 0 to 4,
$R_2$ is:
  the hydrogen atom;
  a lower alkyl radical having 1 to 6 carbon atoms; or
  a phenyl radical which is unsubstituted or substituted by a halogen atom,
$R_3$ is:
  the hydrogen atom;
  a lower alkyl radical having 1 to 6 carbon atoms; or
  a radical —$(CH_2)_n$-phenyl in which the phenyl is unsubstituted or substituted by a halogen atom, n being an integer from 0 to 4, and
p is an integer from 0 to 2.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

Halogen is understood as meaning a chlorine, bromine, iodine or fluorine atom.

The following abbreviations have been used in the description:
Ph: phenyl
phenethyl: 2-phenylethyl
tBu: tert-butyl (1,1-dimethylethyl)
iPr: isopropyl (1-methylethyl)
Me: methyl
Et: ethyl
THF: tetrahydrofuran
Bn: benzyl In one variant, $X_2$ is the hydrogen atom.

In one variant, $X_1$ is the chlorine atom in the 5-position of the indole ring.

In another variant, $X_1$ is the bromine atom in the 5-position of the indole ring.

In another variant, $X_1$ is the fluorine atom in the 5-position of the indole ring.

In one variant, $R_1$ is the hydrogen atom.
In another variant, $R_1$ is a methyl radical.
In another variant, $R_1$ is a benzyl group.
In one variant, $R_2$ is a methyl radical.
In another variant, $R_2$ is the hydrogen atom.
In one variant, $R_2$ is the hydrogen atom.
In one variant, p is equal to zero.

The particularly preferred compounds of the invention are selected from the products of the formulae

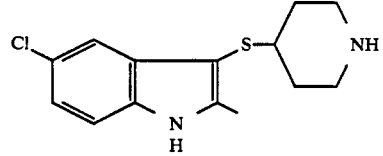

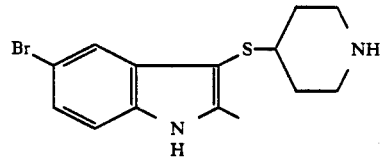

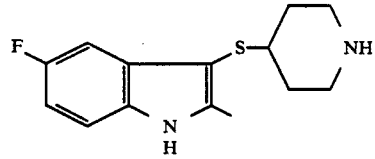

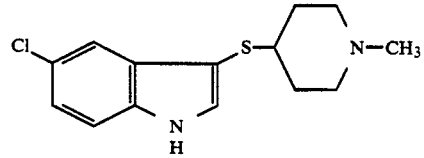

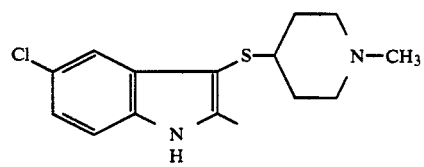

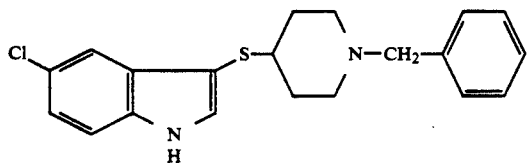

According to the invention, the compounds of formula (I) may be synthesized int he following manner:

Reaction of hydrogen sulfide in an alcohol such as, for example, isopropanol, at a temperature below 15° C., with the piperidin-4-ones of formula (II), followed by reduction with sodium or potassium borohydride in an alcohol such as, for example, isopropanol, will give the piperidine-4-thiols of formula (III) in accordance with the following scheme:

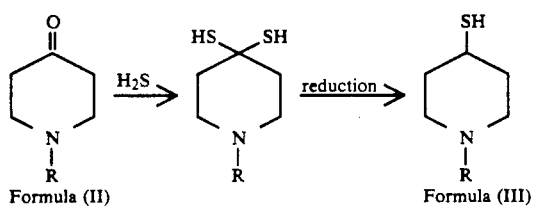

in which formulae (II) and (III), R is a lower alkyl radical having 1 to 6 carbon atoms, a benzyl radical, a phenethyl radical or a protecting group —COOtBu.

The piperidinones of formula (II) are commercially available with the exception of the one in which R= —COOtBu, which is prepared by reacting ditert-butyl dicarbonate with piperidin-4-one or its commercially available monohydrate by the method described in the following literature reference: W. S. SAARI, W. HALCZENKO, J. R. HUFF, J. P. GUARE Jr, C. A. HUNT, W. C. RANDALL, V. J. LOTTI, G. G. YARBROUGH; J. Med. Chem. 1984, 27, 1182-5.

The derivatives of formula (III) in which R is the hydrogen atom will be prepared from the derivatives of formula (III) in which R is a methyl radical by reaction with ethyl chloroformate in acetone, followed by a second treatment with ethyl chloroformate in toluene under reflux and then by a treatment with hydrochloric acid in acetic acid under reflux, in accordance with the following scheme:

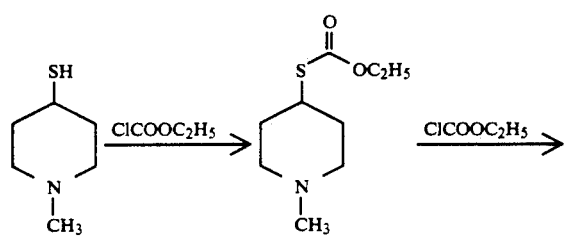

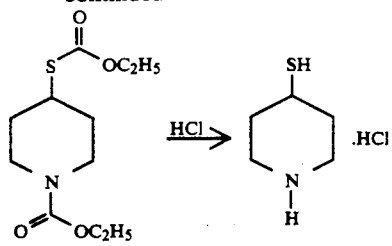

This preparative method is described in the following literature reference:

J. ENGEL, A. BORK, I. NUBERT, H. SCHÖNENBERGER; Arch. Pharm. (Weinheim) 1988, 321, 821-2.

Reaction of the compounds of formula (III), in which R is a lower alkyl radical having 1 to 6 carbon atoms, a benzyl radical, a phenethyl radical, a protecting group —COOtBu or the hydrogen atom, with a halogenoketone of formula (IV):

X—CH$_2$—CO—R'  Formula (IV)

in which R' is a lower alkyl radical having 1 to 6 carbon atoms or a phenyl radical which is unsubstituted or substituted by a halogen atom and X is a halogen atom, optimally chlorine or bromine, will give the derivatives of formula (V):

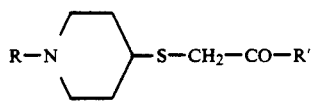

in which R and R' are as defined above.

This reaction is carried out in the presence of a sodium, potassium or lithium alcoholate in the corresponding alcohol or in tetrahydrofuran, or else by phase transfer in the presence of sodium or potassium carbonate and tetrabutylammonium iodide in toluene at temperatures between 20° and 130° C.

Reaction of the same compounds of formula (III) with a halogenoaldehyde whose aldehyde group is protected by ketalization, of formula (VI):

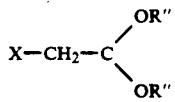

in which R" is a lower alkyl having 1 to 6 carbon atoms, optimally methyl or ethyl, or the two radicals R" together form —CH$_2$—CH$_2$—, and X is a halogen atom, optimally chlorine or bromine, will give the derivatives of formula (VII):

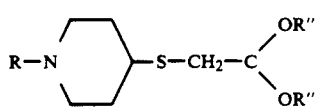

in which R and R" are as defined above.

This reaction is carried out in the same way as for the halogenoketones, for example in the presence of sodium methylate in tetrahydrofuran.

The derivatives of formula (V) or formula (VII) will then be reacted with phenylhydrazines of formula (VIII):

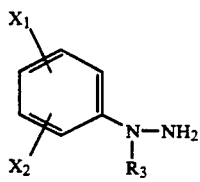

Formula (VIII)

in which $X_1$, $X_2$ and $R_3$ are as defined above.

These phenylhydrazines are commercially available or can be prepared by the conventional methods known to those skilled in the art, for example by the diazotization of commercially available anilines of formula (IX):

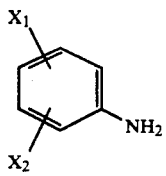

Formula (IX)

in which $X_1$ and $X_2$ are as defined above, with sodium nitrite in an acid medium, followed by treatment of the diazotized derivative with stannous chloride to give a phenylhydrazine of formula (X):

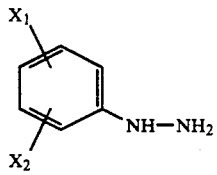

Formula (X)

in which $X_1$ and $X_2$ are as defined above, after which this phenylhydrazine is reacted with halogenated derivatives of formula (XI):

$R_3X$   Formula (XI)

in which $R_3$ is as defined above and X is a halogen atom, in liquid ammonia and/or tetrahydrofuran, in the presence of sodium amide, at a temperature of $-40°$ C., the reaction mixture being left to return to room temperature.

The reaction of the derivatives of formula (V) or formula (VII) with the phenylhydrazines of formula (VIII) will be carried out under the conventional conditions of the Fischer synthesis for indole rings, optimally in the presence of gaseous hydrogen chloride in isopropanol at 0° C. in order to initiate the reaction, which will subsequently be performed at room temperature. This reaction gives the derivatives of formula (XII):

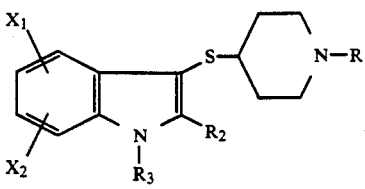

Formula (XII)

in which $X_1$, $X_2$, $R_2$ and $R_3$ are as defined in formula (I), R being a lower alkyl radical having 1 to 6 carbon atoms, a benzyl or phenethyl radical or the hydrogen atom.

When the indole formation reaction is performed with compounds in which R is the group —COOtBu, the compounds of formula (XII) in which R is the hydrogen atom will be obtained directly.

The compounds of formula (XII) in which R is the hydrogen atom may react with halides of formula (XIII):

$R_1X$   Formula (XIII)

which $R_1$ is as defined above and X is a halogen atom, optimally chlorine, bromine or iodine, to give the compounds of formula (I) in which p is equal to zero, this reaction being carried out in the presence of a tertiary base such as triethylamine or pyridine, or sodium or potassium carbonate, in an inert solvent such as toluene, at a temperature between 50° and 130° C.

The compounds of formula (I) in which $R_3$ is the hydrogen atom and p is equal to zero may be alkylated in the 1-position of the indole with the derivatives of formula (XI) by the methods known to those skilled in the art, for example in the presence of a metalating agent such as sodium amide, sodium, potassium or lithium hydride or a sodium, potassium or lithium alcoholate, in a solvent such as liquid ammonia, tetrahydrofuran or dimethylformamide, at a temperature between $-40°$ C. and 80° C., or in the presence of sodium hydroxide and a phase transfer agent in toluene.

The resulting compounds of formula (XIV):

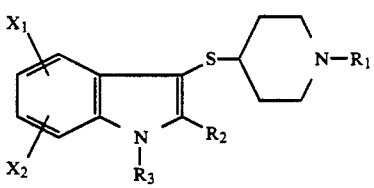

Formula (XIV)

in which $X_1$, $X_2$, $R_1$, $R_2$ and $R_3$ are as defined in formula (I), may be oxidized with an oxidizing agent such as metachloroperbenzoic acid, in a solvent such as chloroform or methylene chloride, at a temperature between 0° and 30° C., to give the compounds of formula (I) in which p is equal to 1 or 2. The amount of oxidizing agent will be chosen so that p=1 or p=2.

The compounds of formula (I) as defined above, and their addition salts, in particular the pharmaceutically acceptable addition salts, possess a very good analgesic activity.

These properties justify their application in therapeutics and the invention further relates, by way of drugs, to the products as defined by formula (I) above, and their addition salts, in particular the pharmaceutically acceptable addition salts.

The addition salts of the compounds of formula (I) can be obtained by reacting these compounds with a mineral or organic acid by a method known per se. Among the acids which can be used for this purpose, there may be mentioned hydrochloric, hydrobromic, sulfuric, phosphoric, toluene-4-sulfonic, methanesulfonic, cyclohexylsulfamic, oxalic, succinic, formic, fumaric, maleic, citric, aspartic, cinnamic, lactic, glutamic, N-acetylaspartic, N-acetylglutamic, ascorbic, malic, benzoic, nicotinic and acetic acids.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal, ocular, nasal or auricular route.

These compositions can be solid or liquid and can be in the pharmaceutical forms commonly used in human medicine, such as, for example, simple or coated tablets, gelatin capsules, granules, suppositories, injectable preparations, transdermal systems, eye lotions, aerosols and sprays, and ear drops. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semi-synthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers a pharmaceutical composition with analgesic activity affording especially a favorable treatment for pain, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with analgesic activity is prepared which affords especially a favorable treatment for pain.

In one variant, a pharmaceutical composition is formulated as gelatin capsules or tablets containing from 1 mg to 1000 mg of active ingredient, or as injectable preparations containing from 0.1 mg to 500 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels or aerosol preparations.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapeutics for the afore-mentioned indications, orally in the form of tablets or gelatin capsules containing from 1 mg to 1000 mg of active ingredient, or parenterally in the form of injectable preparations containing from 0.1 mg to 500 mg of active ingredient, in one or more daily dosage units for an adult with an average weight of 60 to 70 kg.

In animal therapeutics, the daily dose which can be used is between 0.01 and 20 mg per kg.

Further characteristics and advantages of the invention will be understood more clearly from the following description of some Examples, which in no way imply a limitation but are given by way of illustration.

The method described in the literature (H. BARRERA, R. E. LYLE, J. Org. Chem. (1962) 27, 641-2) is used to prepare 1-methylpiperidine-4-thiol (formula III in which R=methyl) and the following thiols:

EXAMPLE 1

1-(Phenylmethyl)piperidine-4 thiol

Formula (III): $R = CH_2Ph$

Oil.

$^1H$ NMR ($CDCl_3$): 7.15-7.4 (m, 5H); 3.48 (s, $CH_2$ benz); 2.65-2.9 (m, 2CH+SCH); 1.9-2.15 (m, 4CH); 1.55-1.75 (m, 2CH); 1.5 (d, SH, J=7 Hz).

EXAMPLE 2

1-(2-Phenylethyl)piperidine-4-thiol

Formula (III): $R = CH_2CH_2Ph$

Oil.

$^1H$ NMR ($CDCl_3$): 7.15-7.35 (m, 5H); 2.9-3.05 (m, 2CH); 2.65-2.9 (m, $CH_2$+SCH); 2.5-2.65 (m, $CH_2$); 1.95-2.25 (m, 4CH); 1.6-1.85 (m, 2CH); 1.54 (d, SH, J=7.1

EXAMPLE 3

1,1-Dimethylethyl 4-mercaptopiperidine-1-carboxylate

Formula (III): $R = CO_2tBu$

Oil.

$^1$H NMR (CDCl$_3$): 155.0 (Cq); 79.7 (Cq); 43.6 (CHS); 36.5 (CH$_2$); 36.1 (CH$_2$); 28.5 (CH$_3$).

EXAMPLE 4

1-(1 Methylethyl)piperidine 4-thiol

Formula (III): R=iPr

Oil.
$^1$H NMR (CDCl$_3$): 2.6–2.9 (m, 4H); 2.1–2.3 (m, 2CH); 1.95–2.1 (m, 2CH); 1.51 (d, SH, J=7.6 Hz); 1.5–1.75 (m, 2CH); 1.02 (d, 2CH$_3$, J=6.5 Hz).

EXAMPLE 5

1-Methyl-4-[(2-oxopropyl)thio]piperidine

Formula (V): R=Me, R'=Me

Sodium methylate (5.9 g) is added in portions to a solution of 1-methylpiperidine-4-thiol (14 g) in anhydrous tetrahydrofuran (100 ml) at room temperature. After 2 hours at this temperature, chloroacetone (8.8 ml) is added dropwise. After 24 hours, the precipitate is filtered off and the filtrate is concentrated and chromatographed on silica gel (eluent: ethyl acetate, then ethanol) to give 1-methyl-4-[(2-oxopropyl)thio]-piperidine (11.5 g) in the form of an oil.

$^1$H NMR (CDCl$_3$): 3.28 (s, CH$_2$S); 2.75–2.90 (m, (2H); 2.5–2.7 (m, CHS); 2.30 (s, CH$_3$N); 2.25 (s, CH$_3$); 1.85–2.15 (m, 4H); 1.5–1.75 (m, 2H).

The following compounds (Examples 6 and 7) were prepared by using the same method with the appropriate chloroketones and piperidine-4-thiols:

EXAMPLE 6

4-[(2-Oxopropyl)thio]piperidine

Formula (V): R=H, R'=Me

Yellow solid: m.p.=136° C.
Hydrochloride: m.p.=118° C.
$^1$H NMR (CDCl$_3$): 3.2 (s, CH$_2$S); 2.95–3.1 (m, 2H); 2.45–2.75 (m, 3H+NH); 2.23 (s, CH$_3$); 1.75–1.95 (m, 2H); 1.25–1.5 (m, 2H).

EXAMPLE 7

4-[[2 (4 Chlorophenyl)-2 oxoethyl]thio]-piperidine

Formula (V): R=H, R'=4-Cl-Ph

Orange solid: m.p.=202° C.
$^1$H NMR (CDCl$_3$): 7.9 (d, 2CH, J=8.5 Hz); 7.43 (d, 2CH, J 8.5 Hz); 3.75 (s, SCH$_2$); 2.95–3.25 (m, 2H+HN); 2.7–2.9 (m, SCH); 2.5–2.7 (m, 2CH); 1.85–2.05 (m, 2CH); 1.35–1.6 (m, 2CH).

EXAMPLE 8

4-[(2-Oxopropyl)thio]-I (phenylmethyl)-piperidine

Formula (V): R=CH$_2$Ph, R'=Me

A suspension of 1-(phenylmethyl)piperidine-4-thiol (70 g, prepared in Example 1), chloroacetone (26.9 ml), sodium carbonate (71.6 g) and tetrabutylammonium iodide (31.2 g) in toluene (350 ml) is stirred at room temperature for 4 hours. The insoluble material is filtered off and washed with toluene. After concentration, the filtrate is taken up in dichloromethane and washed with dilute sodium hydroxide and then with a saturated aqueous solution of sodium chloride. After drying over sodium sulfate, the solution is concentrated to give 4-[(2-oxopropyl)thio]-1-(phenylmethyl) piperidine (82.2 g) in the form of an oil, which is sufficiently pure to be used in the next step.

$^1$H NMR (CDCl$_3$): 7.15–7.35 (m, 5H); 3.5 (s, CH$_2$ benz); 3.2 (s, SCH$_2$); 2.75–2.95 (m, 2H); 2.55–2.75 (m, SCH); 2.28 (s, CH$_3$); 1.85–2.15 (m, 4H); 1.5–1.75 (m, 2CH).

The following compounds (Examples 9 and 10) were prepared by using the same method of synthesis with the appropriate piperidine-4-thiols:

EXAMPLE 9

4-[(2-Oxopropyl)thio]-1-(2-phenylethyl)piperidine

Formula (V): R=CH$_2$CH$_2$Ph, R'=Me

Oil.
$^1$H NMR (CDCl$_3$): 7.1–7.35 (m, 5H); 3.27 (s, SCH$_2$); 2.85–3.05 (m, 2H); 2.75–2.85 (m, 2H); 2.5–2.75 (m, 3H); 2.29 (s, CH$_3$); 1.9–2.2 (m, 4H); 1.5–1.8 (m, 2H).

EXAMPLE 10

1,1-Dimethylethyl 4-[(2 oxopropyl)thio]-piperidine-1-carboxylate

Formula (V): R=CO$_2$tBu, R'=Me

Oil.
$^1$H NMR (CDCl$_3$): 3.9–4.05 (m, 2CH); 3.26 (s, SCH$_2$); 2.7–3 (m, 2CH+SCH); 2.32 (s, CH$_3$); 1.85–2 (m, 2CH); 1.35–1.6 (m, 2CH); 1.45 (s, 3CH$_3$).

EXAMPLE 11

4-[(2,2-Diethoxyethyl)thio]-1-methylpiperidine

Formula (VII): R=Me, R''=Et

Sodium methylate (18.1 g) is added in portions to a solution of 1-methylpiperidine-4-thiol (22 g) in anhydrous tetrahydrofuran (200 ml). After one hour, the diethyl acetal of bromoacetaldehyde (30.3 ml) is added. After 4 hours at room temperature, the solution is heated for 2 hours at 40° C. The insoluble material is filtered off and rinsed with THF. The filtrate is concentrated and then distilled under reduced pressure to give 4-[(2,2-diethoxyethyl)thio]-1-methylpiperidine (36 g; b.p.=104°–108° C. under 0.05 atm) in the form of an oil.

$^1$H NMR (CDCl$_3$): 4.6 (t, 1H, J=5.6 Hz); 3.45–3.8 (m, 2CH$_2$O); 2.65–2.9 (m, 3CH); 2.72 (d, SCH$_2$, J=5.6 Hz); 2.26 (s, NCH$_3$); 1.9–2.1 (m, 4CH); 1.5–1.75 (m, 2CH); 1.22 (t, 2CH$_3$, J=7 Hz).

Compounds 12 and 13 are also prepared by using the same method:

EXAMPLE 12

4-[(2,2-Diethoxyethyl)thio]-1-(phenylmethyl)piperidine

Formula (VII): R=CH$_2$Ph, R''=Et

Oil
$^1$H NMR (CDCl$_3$): 7.2–7.4 (m, 5H); 4.6 (t, 1H, J=5.6 Hz); 3.46 (s, CH$_2$ benz); 3.5–3.8 (m, 2CH$_2$O); 2.65–2.95

(m, 4H); 2.75 (d, SCH$_2$, J=5.6 Hz); 1.85-2.15 (m, 4H); 1.5-1.8 (m, 2H); 1.22 (t, 2CH$_3$, J=7 Hz).

EXAMPLE 13

4-[(2,2-Diethoxyethyl)thio]-1-(1 methylethyl)piperidine

Formula (VII): R=iPr, R''=Et

Oil.

$^1$H NMR (CDCl$_3$): 4.60 (t, 1H, J=5.6 Hz); 3.45-3.75 (m, 2CH$_2$O); 2.6-2.9 (m, 4H); 2.73 (d, CH$_2$S, J=5.6 Hz); 2.1-2.25 (m, 2CH); 1.9-2.05 (m, 2CH); 1.5-1.7 (m, 2CH); 1.22 (t, 2CH$_3$, J=7 Hz); 1.02 (d, 2CH$_3$, J=6.6 Hz).

EXAMPLE 14

2,5-Dimethyl-3-[[1-(phenylmethyl)piperidin-4-yl]thio]-1H-indole hydrochloride

Formula (I): R$_1$ = Bn, R$_2$ = Me, R$_3$ = H,
X$_1$ = 5-Me, X$_2$ = H, p = 0

Paratolylhydrazine hydrochloride (20 g) is added to a solution of 4-[(2-oxopropyl)thio]-1-(phenylmethyl)-piperidine (33.2 g), prepared in Example 8, in isopropanol (150 ml) under nitrogen. After 30 minutes, the solution is cooled to 0° C. and saturated with gaseous hydrogen chloride. After 4 hours at room temperature, the precipitate formed is filtered off, washed with water and then taken up in hot ethanol. After cooling, the white crystals of 2,5-dimethyl-3-[[1-(phenylmethyl)piperidin-4-yl]thio]-1H-indole hydrochloride (28.3 g) are filtered off.

C$_{22}$H$_{26}$N$_2$S.HCl.
M.p.=258° C.

The following compounds (Examples 15 to 32) were prepared by using the same method of synthesis with the appropriate hydrazines and ketones:

EXAMPLE 15

5-Chloro-2-methyl-3-(piperidin-4 ylthio)-1H-indole

Formula (I): R$_1$ = H, R$_2$ = Me, R$_3$ = H,
X$_1$ = 5-Cl, X$_2$ = H, p = 0

Off-white solid.
C$_{14}$H$_{17}$ClN$_2$S.
M.p.=198°-199° C.

EXAMPLE 16

5-Fluoro 2-methyl-3-(piperidin-4-ylthio)-1H-indole

Formula (I): R$_1$ = H, R$_2$ = Me, R$_3$ = H,
X$_1$ = 5-F, X$_2$ = H, p = 0

White solid.
C$_{14}$H$_{17}$FN$_2$S.
M.p.=201° C. (purified by chromatography on silica gel with the following eluent: CHCl$_3$/MeOH/NH$_4$OH : 80/20/1).

EXAMPLE 17

5-Methoxy-2-methyl-3-(piperidin-4 ylthio)-1H-indole

Formula (I): R$_1$ = H, R$_2$ = Me, R$_3$ = H,
X$_1$ = 5-OMe, X$_2$ = H, p = 0

Pale yellow solid.
C$_{15}$H$_{20}$N$_2$OS.
M.p.=217°-218° C. (recrystallized from xylene).

EXAMPLE 18

2-Methyl-3-(piperidin-4-ylthio)-5-(trifluoromethyl)-1H-indole hydrochloride

Formula (I): R$_1$ = H, R$_2$ = Me, R$_3$ = H,
X$_1$ = 5-CF$_3$, X$_2$ = H, p = 0

White solid.
C$_{15}$H$_{17}$F$_3$N$_2$S.HCl.
M.p.=298°-301° C. (recrystallized from water).

EXAMPLE 19

5,7-Dichloro-2-methyl-3-(piperidin-4-yl-thio)-1H-indole hydrochloride

Formula (I): R$_1$ = H, R$_2$ = Me, R$_3$ = H,
X$_1$ = 5-Cl, X$_2$ = 7-Cl, p = 0

Beige solid.
C$_{14}$H$_{16}$Cl$_2$N$_2$S.HCl.
M.p.>275° C.

EXAMPLE 20 b
4,6-Dichloro-2-methyl-3-(piperidin-4-yl-thio)-1H-indole hydrochloride

Formula (I): R$_1$ = H, R$_2$ = Me, R$_3$ = H,
X$_1$ = 4-Cl, X$_2$ = 6-Cl, p = 0

Beige solid.
C$_{14}$H$_{16}$Cl$_2$N$_2$S.HCl.
M.p.>275° C.

EXAMPLE 21

5-Chloro-2-(4-chlorophenyl)-3-(piperidin-4-ylthio)-1H indole

Formula (I): R$_1$ = H, R$_2$ = 4-Cl—Ph, R$_3$ = H,
X$_1$ = 5-Cl, X$_2$ = H, p = 0

Pale yellow solid.
C$_{19}$H$_{18}$Cl$_2$N$_2$S.
M.p.=230°-231° C. (recrystallized from xylene).

EXAMPLE 22

5—Chloro 1-[(4 chlorophenyl)methyl]-2-methyl-3-(piperidin-4 ylthio)-1H-indole

Formula (I): R$_1$ = H, R$_2$ = Me, R$_3$ = 4-Cl—Bn,
X$_1$ = 5-Cl, X$_2$ = H, p = 0

White solid.
C$_{21}$H$_{22}$Cl$_2$N$_2$S.
M.p.=122° C.

EXAMPLE 23

5—Chloro-2-methyl-3-[(1-methylpiperidin-4-yl)thio]-1H-indole

Formula (I):  $R_1$ = Me, $R_2$ = Me, $R_3$ = H,
$X_1$ = 5-Cl, $X_2$ = H, p = 0

Beige solid
$C_{15}H_{19}ClN_2S$.
M.p. 154°–157° C. (recrystallized from cyclohexane).

EXAMPLE 24

5-Fluoro-2-methyl-3-[(1-methylpiperidin-4-yl)thio]-1H-indole

Formula (I):  $R_1$ = Me, $R_2$ = Me, $R_3$ = H,
$X_1$ = 5-F, $X_2$ = H, p = 0

Pale yellow solid.
$C_{15}H_{19}FN_2S$.
M.p.=158°–159° C. (recrystallized from cyclohexane).

EXAMPLE 25

5-Bromo-2-methyl-3-[[1-(phenylmethyl)piperidin-4-yl]thio]-1H-indole hydrochloride Formula (I):  $R_1$ = Bn, $R_2$ = Me, $R_3$ = H,
$X_1$ = 5-Br, $X_2$ = H, p = 0

White solid.
$C_{21}H_{23}BrN_2S.HCl$.
M.p.=266°–267° C.

EXAMPLE 26

5 Chloro-2,7-dimethyl-3-[[1-(phenylmethyl)piperidin-4-yl]thio]-1H-indole hydrochloride Formula (I):  $R_1$ = Bn, $R_2$ = Me, $R_3$ = H,
$X_1$ = 5-Cl, $X_2$ = 7-Me, p = 0

White solid.
$C_{22}H_{25}ClN_2S.HCl$.
M.p. 245°–246° C. (recrystallized from acetonitrile).

EXAMPLE 27

7-Chloro-2-methyl 3-[[1-(phenylmethyl)piperidin-4-yl]thio]-1H-indole

Formula (I):  $R_1$ = Bn, $R_2$ = Me, $R_3$ = H,
$X_1$ = 7-Cl, $X_2$ = H, p = 0

White solid.
$C_{21}H_{23}ClN_2S$.
M.p.=133°–134° C. (recrystallized from ethanol).

EXAMPLE 28

4,7-Dichloro-2-methyl-3-[[1-(phenylmethyl)piperidin-4-yl]thio]-1H-indole hydrochloride Formula (I):  $R_1$ = Bn, $R_2$ = Me, $R_3$ = H,
$X_1$ = 4-Cl, $X_2$ = 7-Cl, p = 0

Beige solid.
$C_{21}H_{22}Cl_2N_2S.HCl$.
M.p.=143°–144° C.

EXAMPLE 29

5-Chloro-1,2-dimethyl-3-[[1-(phenylmethyl)piperidin-4-yl]thio]-1H-indole hydrochloride Formula (I):  $R_1$ = Bn, $R_2$ = Me, $R_3$ = Me,
$X_1$ = 5-Cl, $X_2$ = H, p = 0

White solid.
$C_{22}H_{25}ClN_2S.HCl$.
M.p.=231°–233° C.

EXAMPLE 30

5-Chloro-2-methyl-3-[[1-(2-phenylethyl)piperidin-4-yl]thio]-1H-indole

Formula (I):  $R_1$ = $CH_2CH_2Ph$, $R_2$ = Me, $R_3$ = H,
$X_1$ = 5-Cl, $X_2$ = H, p = 0

Pale yellow solid.
$C_{22}H_{25}ClN_2S$.
M.p.=190°–192° C.

EXAMPLE 31

5-Bromo-2-methyl-3-[[1-(2-phenylethyl)piperidin-4-yl]thio]-1H-indole

Formula (I):  $R_1$ = $CH_2CH_2Ph$, $R_2$ = Me, $R_3$ = H,
$X_1$ = 5-Br, $X_2$ = H, p = 0

White solid.
$C_{22}H_{25}BrN_2S$.
M.p. 188°–189° C. (recrystallized from acetonitrile).

EXAMPLE 32

5-Chloro-1,2-dimethyl-3-[[1-(2-phenylethyl)piperidin-4-yl]thio]-1H-indole

Formula (I):  $R_1$ = $CH_2CH_2Ph$, $R_2$ = Me, $R_3$ = Me,
$X_1$ = 5-Cl, $X_2$ = H, p = 0

White solid.
$C_{23}H_{27}ClN_2S$.
M.p.=136°–137° C. (recrystallized from acetonitrile).

EXAMPLE 33

5—Chloro-3-[[1-(phenylmethyl)piperidin-4-yl]thio]-1H-indole hydrochloride

Formula (I):  $R_1$ = Bn, $R_2$ = H, $R_3$ = H,
$X_1$ = 5-Cl, $X_2$ = H, p = 0

4-Chlorophenylhydrazine hydrochloride (1 g) and 4-[(2,2-diethoxyethyl)thio]-1-(phenylmethyl)piperidine (prepared in Example 12) in isopropanol (20 ml) are stirred at room temperature under nitrogen until a solution is formed. After cooling to 0° C., the solution is saturated with gaseous hydrogen chloride. After 4 hours, the precipitate is filtered off, taken up in sodium hydroxide and extracted with ether and then with ethyl acetate. The combined organic phases are dried over sodium sulfate and concentrated. The residual oil is taken up in a solution of hydrogen chloride in ether to give 5-chloro-3-[[1-(phenylmethyl)piperidin-4-yl]thio]-1H-indole hydrochloride (1.4 g).
White solid.
$C_{20}H_{21}ClN_2S.HCl.0.5H_2O$.

M.p.=158°-160° C.

The following compounds (Examples 34 to 43) were prepared by using the same method of synthesis with the appropriate hydrazines and acetals:

EXAMPLE 34

5-Bromo-3-[[1-(phenylmethyl)piperidin-4-yl]thio]-1H-indole

Formula (I):  $R_1$ = Bn, $R_2$ = H, $R_3$ = H,
$X_1$ = 5-Br, $X_2$ = H, p = 0

White solid.
$C_{20}H_{21}BrN_2S$.
M.p. 134°-135° C. (recrystallized from cyclohexane).

EXAMPLE 35

3-[[1-(Phenylmethyl)piperidin 4-yl]thio]-5-(trifluoromethyl) -1H indole

Formula (I):  $R_1$ = Bn, $R_2$ = H, $R_3$ = H,
$X_1$ = 5-$CF_3$, $X_2$ = H, p = 0

White solid.
$C_{21}H_{21}F_3N_2S$.
M.p. 154°-155° C. (recrystallized from cyclohexane).

EXAMPLE 36

1-Phenyl-3-[[1-(phenylmethyl)piperidin-4-yl]thio]-1H-indole oxalate

Formula (I):  $R_1$ = Bn, $R_2$ = H, $R_3$ = Ph,
$X_1$ = H, $X_2$ = H, p = 0

Beige solid.
$C_{26}H_{26}N_2S.C_2H_2O_4$.
M.p.=193°-194° C. (recrystallized from ether).

EXAMPLE 37

5-Chloro-3-[(1-methylpiperidin-4-yl)thio]-1H-indole

Formula (I):  $R_1$ = Me, $R_2$ = H, $R_3$ = H,
$X_1$ = 5-Cl, $X_2$ = H, p = 0

Off-white solid.
$C_{14}H_{17}ClN_2S$.
M.p. 136°-137° C. (recrystallized from cyclohexane).

EXAMPLE 38

5-Methoxy-3-[(1-methylpiperidin 4-yl)thio]-1H-indole

Formula (I):  $R_1$ = Me, $R_2$ = H, $R_3$ = H,
$X_1$ = 5-OMe, $X_2$ = H, p = 0

Beige solid.
$C_{15}H_{20}N_2OS$.
M.p.=153° C. (recrystallized from isopropanol).

EXAMPLE 39

3-[(1-Methylpiperidin-4 yl)thio]-1H-indole

Formula (I):  $R_1$ = Me, $R_2$ = H, $R_3$ = H,
$X_1$ = H, $X_2$ = H, p = 0

Pale yellow solid.
M.p.=143°-144° C. (recrystallized from cyclohexane).

EXAMPLE 40

5-(1-Methylethyl)-3-[(1-methylpiperidin-4-yl)thio]-1H-indole

Formula (I):  $R_1$ = Me, $R_2$ = H, $R_3$ = H,
$X_1$ = 5-iPr, $X_2$ = H, p = 0

Off-white solid.
M.p.=110° C.

EXAMPLE 41

5-Bromo-3-[(1-methylpiperidin-4-yl)thio]1H-indole

Formula (I):  $R_1$ = Me, $R_2$ = H, $R_3$ = H,
$X_1$ = 5-Br, $X_2$ = H, p = 0

Light beige solid.
M.p.=135°-136° C. (recrystallized from cyclohexane).

EXAMPLE 42

5-Bromo-3-[[1-(1-methylethyl)piperidin-4-yl]thio]-1H-indole

Formula (I):  $R_1$ = iPr, $R_2$ = H, $R_3$ = H,
$X_1$ = 5-Br, $X_2$ = H, p = 0

Beige solid.
$C_{16}H_{21}BrN_2S$.
M.p. 116°-118° C. (recrystallized from acetonitrile).

EXAMPLE 43

5-Chloro-3-[[1-(1-methylethyl)piperidin-4-yl]thio]-1H-indole

Formula (I):  $R_1$ = iPr, $R_2$ = H, $R_3$ = H,
$X_1$ = 5-Cl, $X_2$ = H, p = 0

Light beige solid.
$C_{16}H_{21}ClN_2SD$.
M.p.=123° C. (recrystallized from cyclohexane).

EXAMPLE 44

5-Bromo-2-methyl-3 (piperidin-4 ylthio)-1H-indole

Formula (I):  $R_1$ = H, $R_2$ = Me, $R_3$ = H,
$X_1$ = 5-Br, $X_2$ = H, p = 0

4-Bromophenylhydrazine hydrochloride (11.5 g) is solubilized in a solution of 1,1-dimethylethyl 4-[(2-oxopropyl)thio]piperidine-1-carboxylate (prepared in Example 10) in isopropanol (100 ml) under nitrogen. The solution is cooled to 0° C. and saturated with gaseous hydrogen chloride. After 4 hours at room temperature, the precipitate is filtered off, taken up in sodium hydroxide and extracted with ether and then with methylene chloride. The organic phases are combined, dried over sodium sulfate and concentrated. The solid obtained is taken up in the minimum amount of ether and recrystallized from xylene to give 5-bromo-2-methyl-3-(piperidin-4-ylthio) -1H-indole (9.5 g).

Pale yellow solid.
$C_{14}H_{17}BrN_2S$.
M.p.=207°-208° C.

EXAMPLE 45

5-Chloro-2-methyl-3-[[1-[2-(1H-pyrrol-1-yl) ethyl]piperidin-4-yl]thio]-1H indole

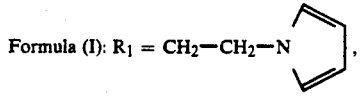

Formula (I): $R_1 = CH_2-CH_2-N$⟨pyrrole⟩, $R_2 = Me, R_3 = H, X_1 = 5\text{-}Cl,$
$X_2 = H, p = 0$ A toluene solution (100 ml) of 5-chloro-2-methyl-3-(piperidin-4-ylthio)-1H-indole (1.09 g, prepared in Example 15), sodium carbonate (0.78 g) and 1-(2-iodoethyl)-1H-pyrrole (0.92 g, prepared according to GALEAZZI, E.; GUZMAN, A.; PINEDO, A.; SALDANA, A.; TORRE, D.; MUCHOWSKI, J. M., Can. J. Chem. (1983) 61, 454–60) is refluxed for 15 hours. The reaction mixture is taken up in a water/dichloromethane mixture. The organic phase is dried over magnesium sulfate and concentrated. The residue is chromatographed on silica gel (eluent: $CH_2Cl_2/MeOH$ : 90/10) to give 5-chloro-2-methyl -3-[[1-[2-(1H-pyrrol-1-yl)ethyl]piperidin-4-yl]thio]-1H-indole (0.9 g).

Off-white solid.
$C_{20}H_{24}ClN_3S$.
M.p.=169°-171° C.

EXAMPLE 46

3-[[1-(Phenylmethyl)piperidin 4-yl]thio]-1,2,5-trimethyl-1H-indole

Formula (I): $R_1 = Bn, R_2 = Me, R_3 = Me,$
$X_1 = 5\text{-}Me, X_2 = H, p = 0$ An aqueous solution (200 ml) of 2,5-dimethyl-3-[[1-(phenylmethyl) piperidin-4-yl]thio]-1H-indole hydrochloride (prepared in Example 14) is rendered basic to pH 9 with sodium hydroxide. After extraction with ether, the organic phase is dried over sodium sulfate and concentrated. The indole crystallizes (10.4 g) after the addition of heptane.

A solution of this indole (10 g) in anhydrous tetrahydrofuran (50 ml) is added dropwise to a solution of sodium amide (1.3 g) in liquid ammonia (20 ml) at −40° C. After 10 minutes, methyl iodide (2 ml) in tetrahydrofuran (50 ml) is added.

After 2 hours at room temperature, 10 ml of water are added. After concentration, the mixture is taken up in water and extracted with ethyl acetate. The organic phase is dried over sodium sulfate and concentrated. 3-[[1-(Phenylmethyl)piperidin-4-yl]thio]-1,2,5-trimethyl-1H-indole (8.3 g) is obtained after recrystallization from ethanol.

White solid.
$C_{23}H_{28}N_2S$.
M.p.=134°-135° C.

EXAMPLE 47

5—Chloro-2-methyl-3-(piperidin-4-ylsulfinyl)-1H-indole

Formula (I): $R_1 = H, R_2 = Me, R_3 = H,$
$X_1 = 5\text{-}Cl, X_2 = H, p = 1$

Metachloroperbenzoic acid (2.79 g) is added in portions to a solution of 5-chloro-2-methyl-3-(piperidin-4-ylthio)-1H-indole (3 g, prepared in Example 15) in dichloromethane (25 ml) at −40° C. After 4 hours at room temperature, the insoluble material is filtered off. The filtrate is washed with sodium hydroxide and then with water. The aqueous phases are extracted with ether and then with ethyl acetate. The organic phases are combined, dried over magnesium sulfate and concentrated. The oily residue obtained is chromatographed on silica gel (eluent: $CH_2Cl_2/MeOH/NH_4OH$ : 90/10/1) to give 5-chloro-2-methyl-3-(piperidin-4-ylsulfinyl)-1H-indole in the form of an oil, which crystallizes on the addition of ether (0.4 g).

Beige solid.
$C_{14}H_{17}ClN_2OS.H_2O$.
M.p.=140°-145° C.

PHARMACOLOGY

The analgesic activity of the products of the Examples was evaluated by the method involving the stretching movements caused by phenylbenzoquinone in mice, described by Siegmund et al. (1957).

Method

The intraperitoneal injection of phenylbenzoquinone causes twisting and stretching movements in mice. Analgesics prevent or reduce this syndrome, which can be considered as the exteriorization of diffuse abdominal pain.

A 0.02% solution of phenylbenzoquinone in water is administered in a volume of 1 ml/100 g.

The products of the Examples are administered orally one hour before the injection of phenylbenzoquinone.

The stretching and twisting movements are counted for each mouse over an observation period of 5 minutes.

Expression of the Results

The results are expressed in the form of the $ID_{50}$, i.e. the dose which makes it possible to obtain a 50% reduction in the number of pain reactions compared with the control animals.

Results

The results are presented in the Table below.

| Product of | 50% inhibitory dose mg/kg p.o. |
| --- | --- |
| Example 15 | 0.8 |
| Example 16 | 5.9 |
| Example 23 | 11 |
| Example 33 | 9.7 |
| Example 37 | 4 |
| Example 44 | 0.7 |

TOXICOLOGY

The preliminary toxicology studies performed show that the products of the Examples do not induce any deleterious effect in rats after the oral absorption of doses which can vary form 30 to 300 mg/kg.

What is claimed is:

1. A piperidinylthioindole compound of formula (I):

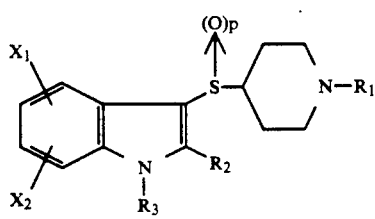

Formula (I)

in which:

X₁ and X₂ are independently:
- a hydrogen atom;
- a halogen atom;
- a lower alkyl radical having 1 to 6 carbon atoms;
- a trifluoromethyl group; or
- a lower O-alkyl radical having 1 to 6 carbon atoms;

and can he located in the 4-, 5-, 6- or 7-position of the indole ring, $R_1$ is:
- a hydrogen atom;
- a lower alkyl radical having 1 to 6 carbon atoms;
- a radical —$(CH_2)_n$-phenyl; or
- a radical —$(CH_2)_n$-pyrrole;

in which n is an integer from 0 to 4, $R_2$ is:
- a hydrogen atom;
- a lower alkyl radical having 1 to 6 carbon atoms; or
- a phenyl radical which is unsubstituted or substituted by a halogen atom, $R_3$ is:
- a hydrogen atom;
- a lower alkyl radical having 1 to 6 carbon atoms; or
- a radical —$(CH_2)_n$-phenyl in which the phenyl is unsubstituted or substituted by a halogen atom, n being an integer from 0 to 4, and p is an integer from 0 to 2, or a pharmaceutically acceptable addition salt thereof.

2. A compound according to claim 1 wherein X₂ is a hydrogen atom and X₁ is a halogen atom and is located in the 5-position of the indole.

3. A compound according to claim 1 wherein $R_1$ is a hydrogen atom, a methyl radical or a benzyl group.

4. A compound according to claim 1 wherein $R_2$ is a hydrogen atom or a methyl radical.

5. A compound according to claim 1 wherein $R_3$ is a hydrogen atom.

6. A compound according to claim 1 wherein p is equal to zero.

7. A compound according to claim 1 which is selected from the derivatives of the formulae:

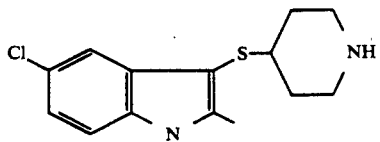
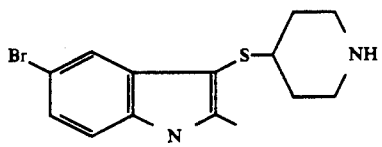
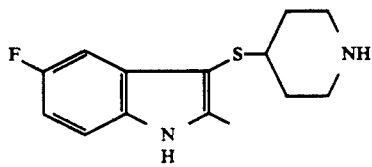
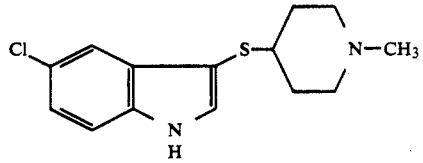
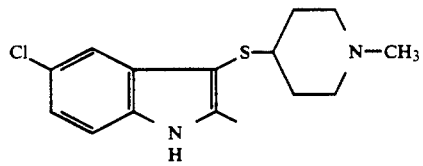
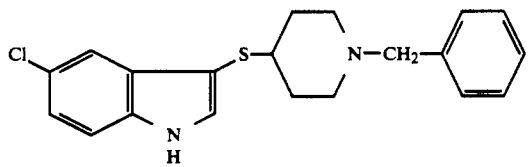

8. A pharmaceutical composition with analgesic activity, which contains a pharmaceutically effective amount of a compound of formula (I) as defined in claim 1, or a pharmaceutically acceptable addition salt thereof, incorporated in a pharmaceutically acceptable excipient, vehicle or carrier.

9. A pharmaceutical composition according to claim 8, which is formulated as a gelatin capsule or a tablet containing form 1 mg to 1000 mg of active ingredient.

10. A pharmaceutical composition according to claim 8, which is formulated as an injectable preparations containing from 0.1 to 500 mg of active ingredient.

11. A method of therapeutic treatment of mammals for pain, which comprises administering to this mammal a therapeutically effective amount of a compound of formula (I) as defined in claim 1 or one of its pharmaceutically acceptable addition salt.

* * * * *

UNITED STATES PATENT AND TRADEMARK OFFICE
CERTIFICATE OF CORRECTION

PATENT NO. : 5,317,025

DATED : May 31, 1994

INVENTOR(S) : Nicole Bru-Magniez et al

It is certified that error appears in the above-identified patent and that said Letters Patent is hereby corrected as shown below:

On title page, item [73]

After "Assignee:", change "Laboratoires USPA" to

--Laboratoires UPSA--.

Signed and Sealed this

Twenty-seventh Day of September, 1994

Attest:

BRUCE LEHMAN

Attesting Officer     Commissioner of Patents and Trademarks